(12) United States Patent
Miyashita

(10) Patent No.: US 9,076,078 B2
(45) Date of Patent: Jul. 7, 2015

(54) IMAGE PROCESSING APPARATUS, METHOD AND PROGRAM FOR DETERMINING ARRANGEMENT OF VECTORS ON A DISTRIBUTION MAP

(75) Inventor: Naoyuki Miyashita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1009 days.

(21) Appl. No.: 12/485,182

(22) Filed: Jun. 16, 2009

(65) Prior Publication Data

US 2009/0309961 A1    Dec. 17, 2009

(30) Foreign Application Priority Data

Jun. 16, 2008    (JP) .................................. 2008-157223

(51) Int. Cl.
*G06K 9/62*    (2006.01)
*G06T 7/40*    (2006.01)
(Continued)

(52) U.S. Cl.
CPC ................ *G06K 9/6256* (2013.01); *G06K 9/62* (2013.01); *G06K 9/6255* (2013.01);
(Continued)

(58) Field of Classification Search
CPC .................... G06F 17/30256; G06F 17/30843; G06F 19/34; G07F 9/00718; G07F 9/00744; G07F 9/00751; A61B 2019/5265; G06T 7/0012; H04N 21/8453; H04N 21/8456; H04N 21/845; G06K 9/62; G06K 9/6255; G06K 9/6256; G06K 9/6257; G06K 9/6259
See application file for complete search history.

(56) References Cited

U.S. PATENT DOCUMENTS 5,963,670 A * 10/1999 Lipson et al. .................. 382/224
6,331,116 B1 * 12/2001 Kaufman et al. ............. 434/262
(Continued)

FOREIGN PATENT DOCUMENTS

JP    2000-285141    10/2000
JP    2002-041545    2/2002
(Continued)

OTHER PUBLICATIONS

F. Vilariño, P. Spyridonos, J. Vitrià, C. Malagelada, & P. Radeva, "A Machine Learning Framework Using SOMs: Application in the Intestinal Motility Assessment", 4225 Lecture Notes in Comp. Sci. 188-97 (Nov. 2006).*

(Continued)

*Primary Examiner* — David N Werner
(74) *Attorney, Agent, or Firm* — Scully, Scott, Murphy & Presser, P.C.

(57) ABSTRACT

There is provided an image processing apparatus that includes a feature data calculating unit, a distribution map generating unit, and a display control unit. The feature data calculating unit calculates feature data of each image contained in a group of sequential images that are taken by an image taking apparatus. The distribution map generating unit includes a representative vector calculating unit and a representative vector arrangement determining unit, and generates a distribution map that represents an overall trend of the group of sequential images. The representative vector calculating unit calculates a predetermined number of representative vectors that represent a plurality of images contained in the group of sequential images. The representative vector arrangement determining unit determines arrangement of the calculated representative vectors on the distribution map. The display control unit displays the distribution map on a display unit.

22 Claims, 16 Drawing Sheets

(51) Int. Cl.
   *H04N 5/232*   (2006.01)
   *G06F 19/00*   (2011.01)

(52) U.S. Cl.
   CPC ........... *G06K 9/6257* (2013.01); *G06K 9/6259* (2013.01); *G06F 19/321* (2013.01); *G06K 9/6251* (2013.01); *G06K 9/6253* (2013.01); *G06K 2209/05* (2013.01); *G06T 7/40* (2013.01); *G06T 2207/10068* (2013.01); *G06T 2207/20021* (2013.01); *G06T 2207/30028* (2013.01); *G06T 2207/30092* (2013.01); *H04N 5/23229* (2013.01)

(56) References Cited

U.S. PATENT DOCUMENTS

| | | | | |
|---|---|---|---|---|
| 6,331,859 | B1 * | 12/2001 | Crinon | 345/619 |
| 7,016,540 | B1 * | 3/2006 | Gong et al. | 382/225 |
| 7,280,694 | B2 * | 10/2007 | Kim et al. | 382/181 |
| 7,346,209 | B2 * | 3/2008 | Gokturk et al. | 382/159 |
| 8,600,126 | B2 * | 12/2013 | Morita | 382/128 |
| 2004/0258285 | A1 * | 12/2004 | Hansen et al. | 382/128 |
| 2005/0147203 | A1 * | 7/2005 | Ross et al. | 378/19 |
| 2006/0074275 | A1 * | 4/2006 | Davidson et al. | 600/160 |
| 2009/0092313 | A1 * | 4/2009 | Negi | 382/160 |
| 2009/0285473 | A1 * | 11/2009 | Li et al. | 382/159 |

FOREIGN PATENT DOCUMENTS

| | | |
|---|---|---|
| JP | 2004-164608 | 6/2004 |
| JP | 2004-321603 | 11/2004 |

OTHER PUBLICATIONS

M.J. Pickering, S.M. Rüger, & D. Sinclair, "Video Retrieval by Feature Learning in Key Frames", 2383 Lecture Notes in Computer Sci. 309-317 (Jul. 4, 2002).*

Japanese Office Action dated Mar. 5, 2013 in related Japanese Patent Application No. 2008-157223.

* cited by examiner

IMAGE PROCESSING APPARATUS, METHOD AND PROGRAM FOR DETERMINING ARRANGEMENT OF VECTORS ON A DISTRIBUTION MAP

CROSS-REFERENCE TO RELATED APPLICATIONS

This application is based upon and claims the benefit of priority from Japanese Patent Application No. 2008-157223, filed on Jun. 16, 2008, the entire contents of which are incorporated herein by reference.

BACKGROUND OF THE INVENTION

1. Field of the Invention

The present invention relates to an image processing apparatus for selecting a representative image from a group of sequential images that are taken by an image taking apparatus such as a capsule endoscope and for displaying the representative image; an image processing method; and an image processing program.

2. Description of the Related Art

Capsule endoscopes are commonly used as means of taking in-vivo images. A capsule endoscope takes images of internal organs at 2 to 4 fps for about 8 hours from when it is swallowed by a subject who is a patient until it is naturally discharged. The images are taken while the capsule endoscope moves through the stomach, the small intestine, and the large intestine due to peristalsis in the alimentary canal. The number of in-vivo images that the capsule endoscope takes in one examination can be up to about 60,000.

As described in, for example, Japanese Patent Application Laid-open No. 2004-321603, in general, the in-vivo images that are taken by a capsule endoscope are reproduced and displayed chronologically as if reproducing a moving image and are observed. An image processing apparatus is known as well that selects a predetermined number of representative images from a group of sequential images and displays the representative images to represent the overall trend of the group of sequential images. For example, the image processing apparatus described in "A Machine Learning Framework Using SOMs: Application in the Intestinal Motility Assessment" uses SOM (Self Organized Maps) to select representative images from a group of sequential in-vivo images and to display the representative images.

SUMMARY OF THE INVENTION

An image processing apparatus according to an aspect of the present invention includes a feature data calculating unit that calculates feature data of each image contained in a group of sequential images that are taken by an image taking apparatus; a distribution map generating unit that generates a distribution map that represents an overall trend of the group of sequential images; and a display control unit that displays the distribution map on a display unit. The distribution map generator includes a representative vector calculating unit that calculates a predetermined number of representative vectors that represent a plurality of images contained in the group of sequential images based on the feature data of the each image and a level of importance of the each image; and a representative vector arrangement determining unit that determines arrangement of the calculated representative vectors on the distribution map.

An image processing method according to another aspect of the present invention includes calculating feature data of each image contained in a group of sequential images that are taken by an image taking apparatus; generating a distribution map that represents an overall trend of the group of sequential images; and displaying the distribution map on a display unit. The generating includes calculating a predetermined number of representative vectors that represent a plurality of images contained in the group of sequential images based on the feature data of the each image and a level of importance of the each image; and determining arrangement of the calculated representative vectors on the distribution map.

A computer program product according to still another aspect of the present invention has a computer readable medium including programmed instructions. The instructions, when executed by a computer, cause the computer to perform the above-described method.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
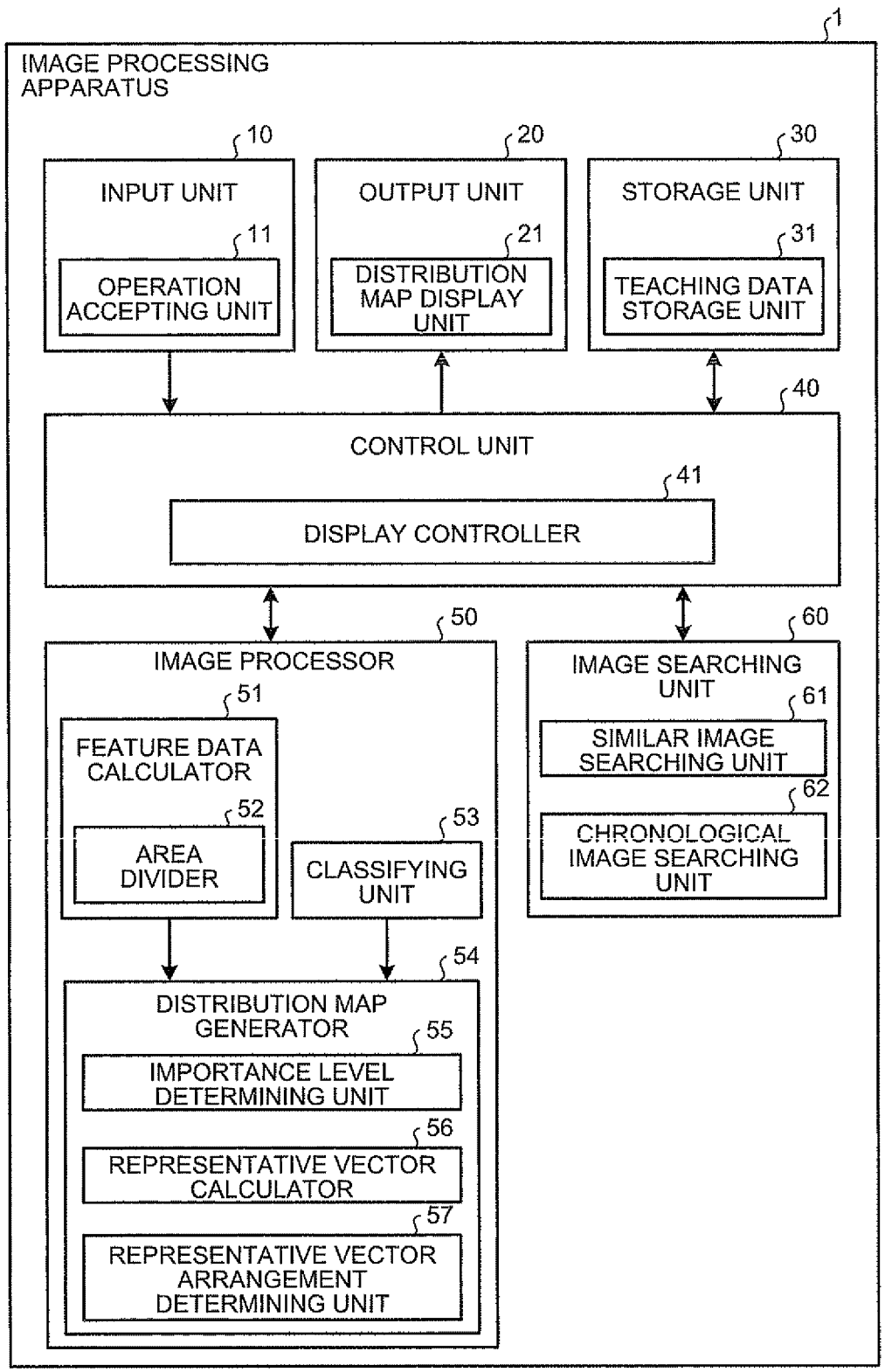
FIG. 1 is a block diagram of a schematic configuration of an image processing apparatus according to a first embodiment of the present invention.

Preferred embodiments of an image processing apparatus, an image processing method, and an image processing program according to the present invention are explained below with reference to the accompanying drawings. The embodiments are explained, taking as an example an image processing apparatus that processes a group of sequential in-vivo images up to 60,000 that are taken chronologically by a capsule endoscope, which is an in-vivo image taking apparatus, and displays an image distribution map that represents an overall trend of a case. Note that a group of images to be processed by the image processing apparatus according to the present invention is not limited to a group of images that are taken by a capsule endoscope. In addition, the embodiments do not limit the present invention. The same parts or corresponding parts in the drawings are denoted by the same reference numerals.

(First Embodiment)

An image processing apparatus according to a first embodiment is explained below with reference to FIG. 1. FIG. 1 is a block diagram of a schematic configuration of an image processing apparatus 1 according to the first embodiment. The image processing apparatus 1 is, for example, a computer, such as a workstation. The image processing apparatus 1 includes an input unit 10 that receives inputs of various types of information; an output unit 20 that displays and outputs various types of information, such as a process result; a storage unit 30 that stores therein various types of information, such as information about a group of sequential images; and a control unit 40 that controls processes and operations of each unit of the image processing apparatus 1. The image processing apparatus 1 further includes an image processor 50 that processes a group of sequential images that are taken chronologically by a capsule endoscope; and an image searching unit 60 that searches a predetermined image from the group of sequential images.

The input unit 10 includes a key board, a mouse, and a data communication interface. The input unit 10 receives inputs of various types of information directly from an observer and receives inputs of image information about in-vivo images through, for example, a portable recording medium, such as various types of memory card, CD, and DVD, or a communication network. The input unit 10 includes an operation accepting unit 11. The operation accepting unit 11 accepts an operation for selecting an image that is displayed on the output unit 20.

The output unit 20 is a display device that constitutes a display unit, such as a liquid crystal display. The output unit 20 displays a result of image processing that is performed by the image processor 50 and a result of image searching that is performed by the image searching unit 60. The output unit 20 also displays a GUI (Graphical User Interface) screen for requesting an observer to input various types of processing information. The output unit 20 includes a distribution map display unit 21 as an example of a display screen. The distribution map display unit 21 displays a distribution map that represents the overall trend of the group of sequential images.

The storage unit 30 includes a hard disk, a ROM, and a RAM. The storage unit 30 stores therein various type of information, such as various processing programs that the control unit 40 is caused to execute and processing results. The storage unit 30 includes a teaching data storage unit 31 and previously stores teaching data that is used in a process for classifying a group of sequential images into predetermined types and in a process for setting a level of importance of each image.

The control unit 40 is a CPU. The control unit 40 controls processes and operations of each unit of the image processing apparatus 1 by executing various processing programs that are stored in the storage unit 30. Specifically, the control unit 40 executes an image processing program to cause the image processor 50 to perform a procedure of image processing according to the first embodiment. The control unit 40 includes a display controller 41. The display controller 41 performs control to arrange a predetermined image on a distribution map and to display the distribution map on the distribution map display unit 21.

The image processor 50 includes a feature data calculator 51, a classifying unit 53, and a distribution map generator 54. The image processor 50 performs a process for generating a distribution map.

The feature data calculator 51 calculates feature data of each image contained in the group of sequential images. Specifically, the feature data calculator 51 includes an area divider 52. The area divider 52 divides an image area of each image based on a state of a unique image taking target in the body. For example, the area divider 52 divides each image into areas, such as a mucous membrane area, a lesion area, a villus area, a bubble area, and a food residue area. The feature data calculator 51 calculates, as feature data of each image, an assembly of numerical values that represent states of their respective divided areas.

The classifying unit 53 performs a process of classifying each image into a predetermined type, for example, a mucous membrane image, a lesion image, a mucous membrane/lesion image, or a bubble/food residue image, based on the feature data of each image and the teaching data. For example, the classifying unit 53 plots feature data of each image and feature data of the teaching data of each image in a feature space to obtain a Euclidean distance, and defines that a type to which teaching data that is most close to an image belongs is a type of the image. The classifying unit 53 also stores, in the storage unit 30, a Euclidean distance between each image and teaching data of each type, i.e., information that represents how much each image is similar to teaching data of each type, in combination with the type of each image.

The distribution map generator 54 performs a process for generating a distribution map that represents an overall trend of the group of sequential images. It suffices that the overall trend of the group of sequential images represents ratios of different types of images to the whole group of images. In addition, it suffices that the distribution map that is generated by the distribution map generator 54 can represent the overall trend of the group of sequential images such that they can be visually recognized. In the embodiment, for example, a two-dimensional distribution map is used. The distribution map generator 54 includes an importance level determining unit 55, a representative vector calculator 56, and a representative vector arrangement determining unit 57. The importance level determining unit 55 determines a level of importance of each image from a Euclidean distance between feature data of each image and feature data of teaching data. The smaller an Euclidean distance between an important image and the teaching data is, the higher the importance level determining unit 55 sets a level of importance. Specifically, the importance level determining unit 55 determines a level of importance of each image depending on a type of each image that is classified by the classifying unit 53. For example, the importance level determining unit 55 determines that a level of importance of an image necessary for diagnosis, for example, a lesion image is high, and determines that a level of importance of an image in which mucous membrane is hard to see, for example, a bubble/food residue image is low. Specific numerical values of levels of importance of the respective types of images are previously stored in the storage unit 30.

Figure 2:
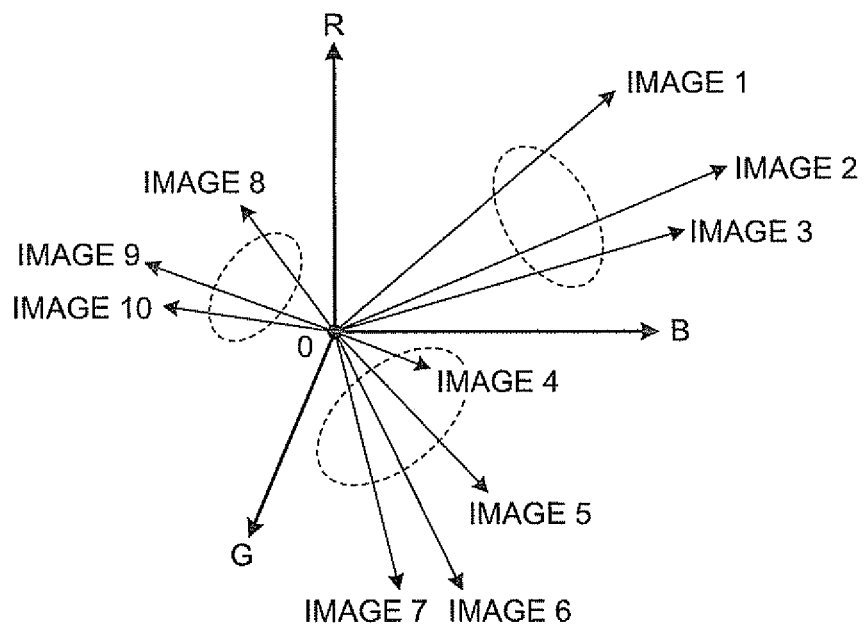
FIG. 2 is a diagram in which feature data of each image is plotted in a feature space and displayed in a vector.
Figure 3:
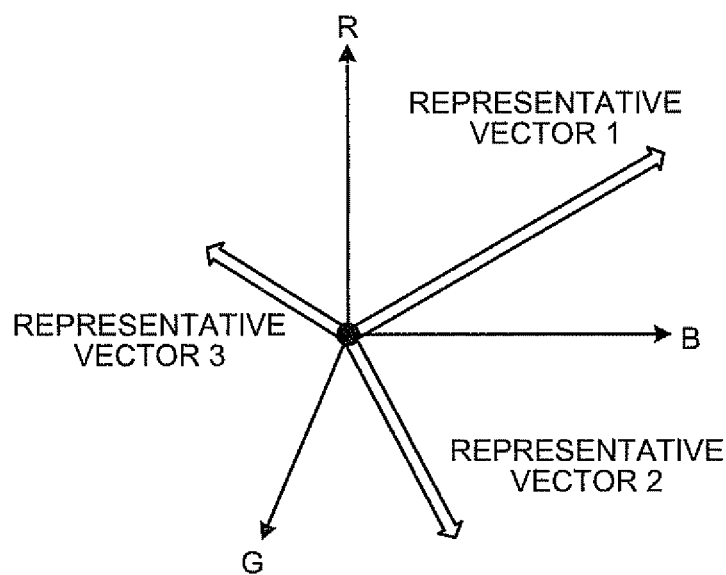
FIG. 3 is a diagram of representative vectors of a group of images shown in FIG. 2.

The representative vector calculator 56 calculates a predetermined number of representative vectors that are set beforehand based on feature data and a level of importance of each image. The representative vector has feature data that represents feature data of a plurality of images and has feature data in the same dimension as that of feature data of each image. A principle of a process that the representative vector calculator 56 performs is explained with reference to FIGS. 2 and 3. FIGS. 2 and 3 represent a case where the number of images of a group of sequential images is 10 and feature data of respective images are three-dimensional. FIG. 2 is a diagram in which pieces of feature data of images 1 to 10 are plotted in, for example, an RGB three-dimensional space and the pieces of feature data of the respective images are displayed in vectors. As shown in FIG. 2, vectors that represents pieces of feature data of the images 1 to 3 are closely positioned, vectors that represents pieces of feature data of the images 4 to 7 are closely positioned, and vectors that represents pieces of feature data of the images 8 to 10 are in neighboring positions. This represents that the images 1 to 3 are similar images, the images 4 to 7 are similar images, and the images 8 to 10 are similar images. If the levels of importance of the 10 images are equal and the number of representative vectors to be calculated with respect to the 10 images is three, the representative vector calculator 56 calculates a representative vector 1 that represents the images 1 to 3, a representative vector 2 that represents the images 4 to 7, and a representative vector 3 that represents the images 8 to 10.

When a representative vector that represents a group of images with high levels of importance, i.e., a representative vector that is similar to feature data of an image with a high level of importance, is not calculated, the representative vector calculator 56 calculates a representative vector that represents the group of images with high levels of importance even if the number of images constituting the group of images with high levels of importance is small, and the representative vector calculator 56 adds at least one vector that represents the images with high levels of importance.

Figures 4, 5:
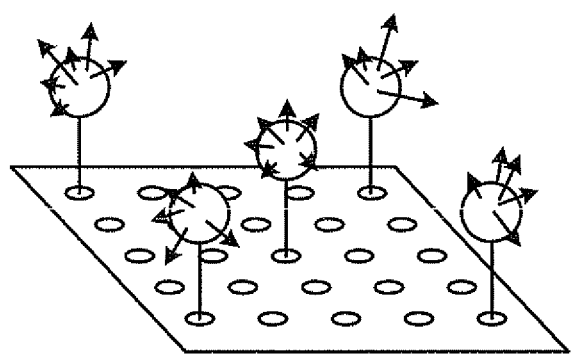
FIG. 4 is a diagram of an example of arrangement of representative vectors.
FIG. 5 is a schematic diagram of representative vectors on a distribution map.

The representative vector arrangement determining unit 57 determines arrangement of the respective representative vectors on a distribution map. In the first embodiment, the representative vectors are arranged on the two-dimensional coordinate system that is referred to as distribution map, so that the overall tendency of the group of sequential images, which is input, is represented. FIG. 4 represents an example of arrangement of representative vectors in a case where the number of representative vectors to be calculated is 25. In the case represented in FIG. 4, a distribution map is formed by arranging the representative vectors in a matrix of 5×5 on a two-dimensional coordinate system. FIG. 5 is a schematic diagram of representative vectors that are arranged on the distribution map. As shown in FIG. 5, each representative vector has high-dimensional feature data and is arranged in a predetermined position depending on the feature data. Therefore, to know which representative vector corresponds to which image, it suffices that high-dimensional feature data of each vector is compared to feature data of each image. The display controller 41 searches the group of images for images whose feature data are most similar to feature data of their respective representative vectors, and arranges the images searched for as representative images in corresponding positions of the respective representative vectors, so as to display the image on the distribution map display unit 21. Accordingly, an intended distribution map that represents the overall trend is obtained.

The image searching unit 60 includes a similar image searching unit 61 and a chronological image searching unit 62, and searches a group of sequential images for a predetermined group of images. Specifically, the similar image searching unit 61 searches for an image that is similar to a selected representative image selected through the operation accepting unit 11. The chronological image searching unit 62 searches for images that are taken chronologically in a predetermined time range based on the selected representative image. The display controller 41 displays the images searched for by the image searching unit 60 on the output unit 20 in addition to the representative image.

Figure 6:
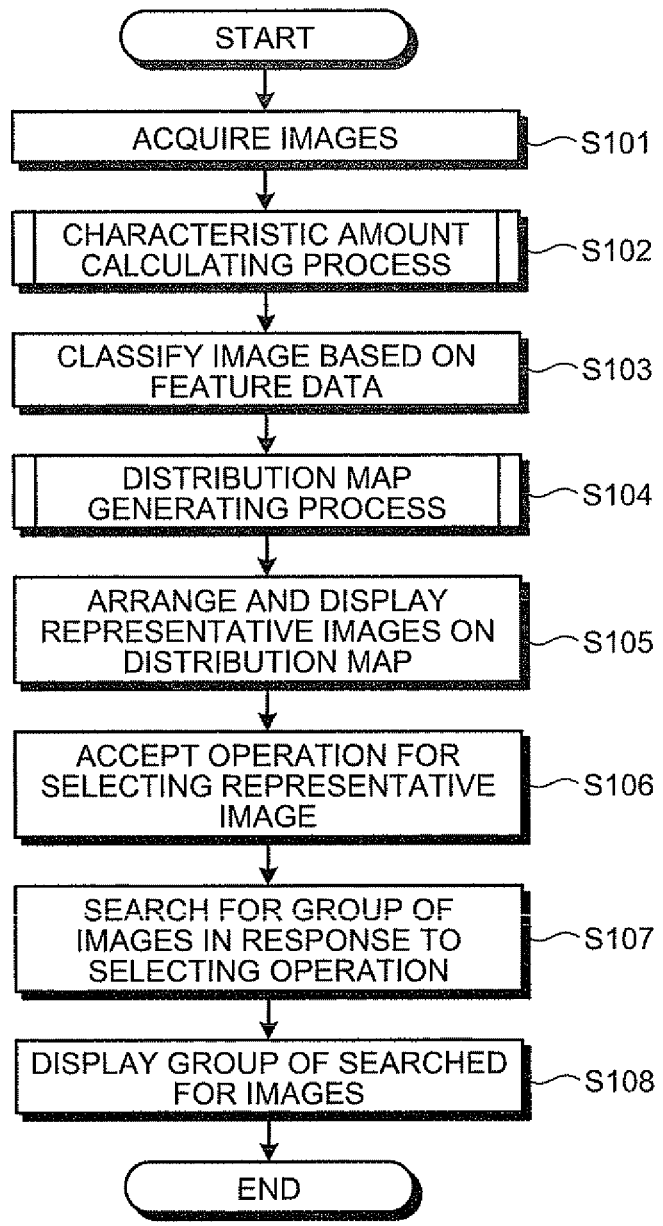
FIG. 6 is a schematic flowchart of a procedure of image processing.

The procedure of the image processing of the image processing apparatus 1 is explained below. FIG. 6 is a schematic flowchart of the procedure of the image processing that is performed by the control unit 40. As shown in FIG. 6, the control unit 40 acquires image data of a group of sequential images that are taken by the capsule endoscope and recorded in the portable recording medium (step S101) and performs a process for calculating feature data of each image (step S102). Thereafter, the control unit 40 classifies each image into, for example, a mucous membrane image, a lesion image, or a bubble/food residue image based on the feature data (step S103). Furthermore, based on the feature data of all images of the group of sequential images, the control unit 40 performs the process for generating a distribution map (step S104). Thereafter, the display controller 41 performs a process for displaying the distribution map in which representative images are arranged in corresponding positions of their respective vectors on the distribution map display unit 21 (step S105).

Thereafter, the control unit 40 controls the operation accepting unit 11 to accept an operation for selecting a representative image (step S106). When the selecting operation is input, the control unit 40 performs a process for searching for a group of images in response to the selecting operation (step S107). Thereafter, the display controller 41 performs a process for displaying the group of images searched for (step S108). Through steps S101 to S108, the control unit 40 generates the distribution map of the group of sequential images, displays the representative images, accepts an operation for selecting images, and performs the process for displaying the group of images that are required by the observer.

Figure 7:
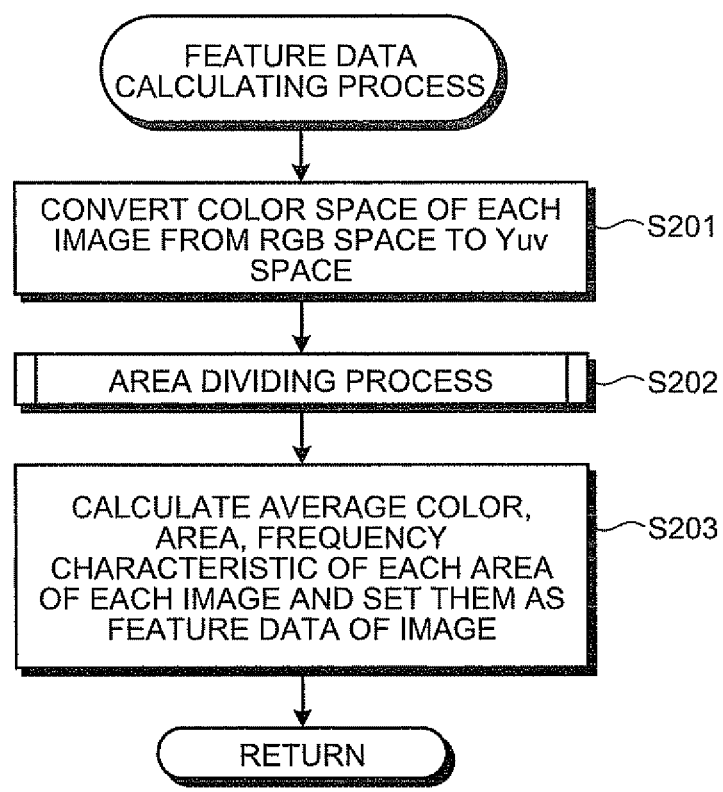
FIG. 7 is a schematic flowchart of a procedure of a feature data calculating process.

First, the feature data calculating process at step S202 is explained below. FIG. 7 is a schematic flowchart of a procedure of the feature data calculating process that is performed by the feature data calculator 51 under the control of the control unit 40. First, the feature data calculator 51 converts a color space of each image from an RGB space to a Yuv space to separate brightness components and color components of an input image (step S201). Thereafter, the area divider 52 performs a process for dividing an image area of each image based on pixel values (step S202). Thereafter, the feature data calculator 51 calculates numerical values of average color, area, and frequency characteristic of each area of each image, and sets an assembly of the calculated numerical values as feature data for each image (step S203). An area of each area is calculated based on a ratio of the number of plots in each area, which is to be described below, to the total number of plots. By setting the values as feature data of each image, the feature data that derives from the internal environment of the body, such as mucous membrane, lesion, villus, bubble, and food residue, can be calculated. The feature data calculator 51 performs the processes of steps S201 to S203 at step S102 to calculate feature data of each image.

At step S201, a color space of each image is converted to a Yuv space to separate brightness components and color components of each input image. As long as brightness components and color components of an image are obtained, the color space after conversion is not limited to a Yuv space. For example, the color space may be converted into a uniform color space, for example, L*a*b* or HSV. Furthermore, instead of conversion on a pixel basis, DC components of DCT coefficients that are used for JPEG encoding may be used.

At step S202, the area divider 52 clusters pixels depending on whether an image taking target in each pixel is mucous membrane, lesion or bubble/food residue based on a pixel value, and divides the image area, regarding an assembly of a plurality of adjacent pixels that belong to the cluster as one area.

Figure 8:
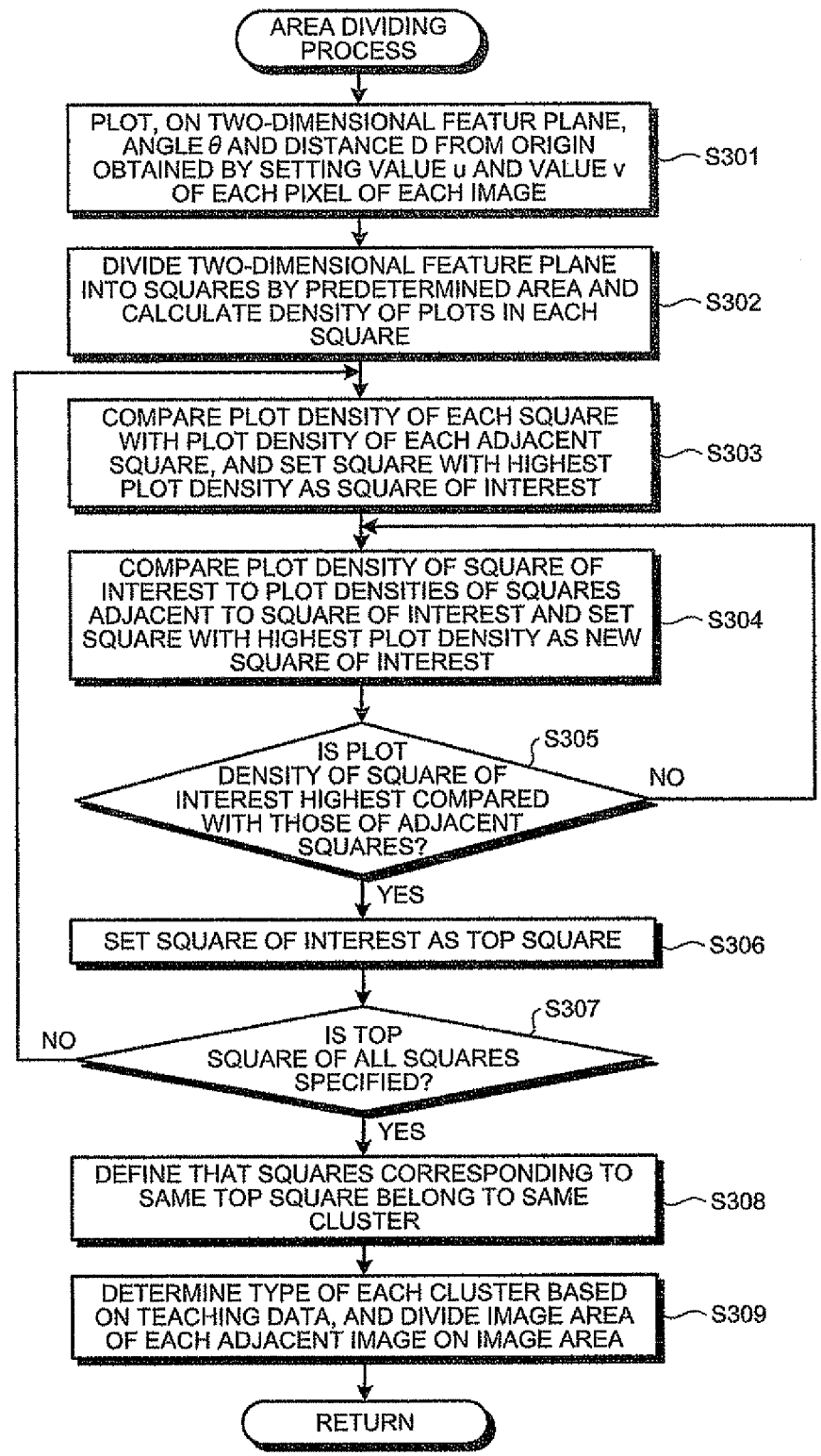
FIG. 8 is a schematic flowchart of a procedure of an area dividing process.

FIG. 8 is a schematic flowchart of a procedure of an area dividing process. As represented in FIG. 8, the area divider 52 plots, on a two-dimensional feature plane, an angle θ and a distance D from an origin obtained by setting a value u and a value v of each pixel of each image are set as two-dimensional vectors (step S301). The area divider 52 divides the two-dimensional feature plane into squares by a predetermined area and calculates a density of plots in each square (step S302).

Thereafter, the area divider 52 regards each square as a start square, compares a plot density of a start square and a plot density of a square adjacent to the start square, and sets a square with the highest plot density as a square of interest of start squares (step S303). The area divider 52 further compares the plot density of the square of interest to plot densities of squares to which the square of interest is adjacent, and sets a square with a high plot density as a new square of interest of the start squares (step S304). Thereafter, the area divider 52 compares the plot density of the square of interest and plot densities of squares that are adjacent to the square of interest (step S305). When there is a square with a plot density higher than that of the square of interest (NO at step S305), the area divider 52 returns to step S304 and repeats the process. In contrast, when the plot density of the square of interest is the highest among the adjacent squares (YES at step S305), the area divider 52 sets the square of interest as a top square (step S306). Thereafter, the area divider 52 checks whether a top square of all squares is specified (step S307). The area divider 52 repeats the processes of steps S303 to S307 until a top square of all squares is specified (NO at step S307).

After a top square of all squares is specified (YES at step S307), the area divider 52 defines that squares corresponding to the same top square belong to the same cluster (step S308). Thereafter, the area divider 52 uses the teaching data to determine a type of each cluster, i.e., a type of pixels that are plotted in squares that belong to a corresponding cluster, and to determine a state of an image taking target that is taken in each pixel, divides an image area of each image into a mucous membrane area, a lesion area, a villus area, and a bubble/food residue area (step S309), and completes the area dividing process. The area divider 52 divides an image area of each image through steps S301 to S309. In the first embodiment, the area divider 52 clusters pixels using the known hill climbing. Alternatively, a clustering method other than the hill climbing may be applied.

Figure 9:
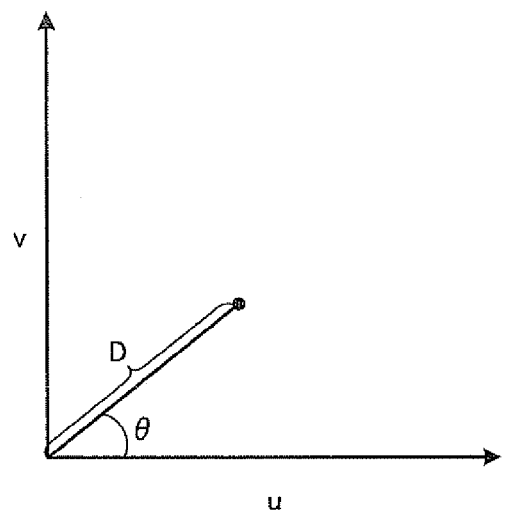
FIG. 9 is a diagram that represents a relation between a value u and a value v and a relation between an angle $\theta$ and a distance D.

At step S301, not a value u and a value v but an angle θ and a distance D are used as feature data of each pixel. FIG. 9 is a diagram that represents a relation between a value u and a value v and a relation between an angle θ and a distance D. When a value u and a value v of an image, which is taken by the capsule endoscope, are used directly as feature data of each pixel and plotted on a two-dimensional feature plane, the plots tend to spread radially on the origin. For this reason, in the first embodiment, converting the value u and the value v to the angle θ and the distance D makes it possible to accurately cluster even plots that are close to the origin.

Figure 10:
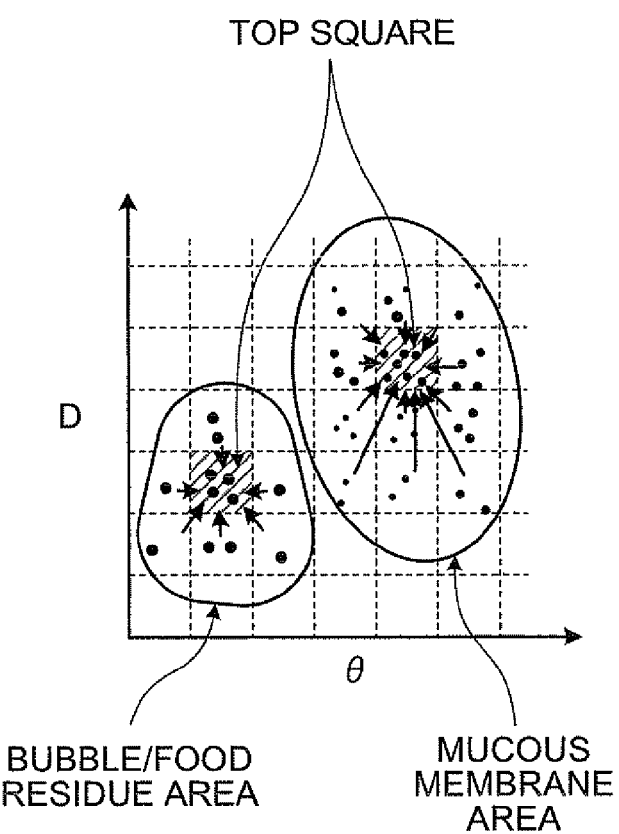
FIG. 10 is a diagram in which an angle $\theta$ and a distance D of each pixel are plotted on a two-dimensional feature plane.

FIG. 10 is a diagram in which an angle θ and a distance D of each pixel are plotted on a two-dimensional plane. In FIG. 10, the square that is positioned at the tips of arrows extending from respective squares is the top square. As represented in FIG. 10, at step S309, it is assumed that squares corresponding to the same top square belong to the same area. An image that is taken by the capsule endoscope has a tendency that a mucous membrane area is plotted on a high-angle side and a bubble/food residue area is plotted on a low-angle side. It is assumed that plots that are largely out of a color range of general mucous membrane (normal mucous membrane) in the mucous membrane area are a lesion area of the image. If an amount of change in value of a pixel from those of a portion that is assumed as a lesion in the image is lager than those of surrounding pixels, it is assuredly determined that the portion is a lesion.

Figure 11:
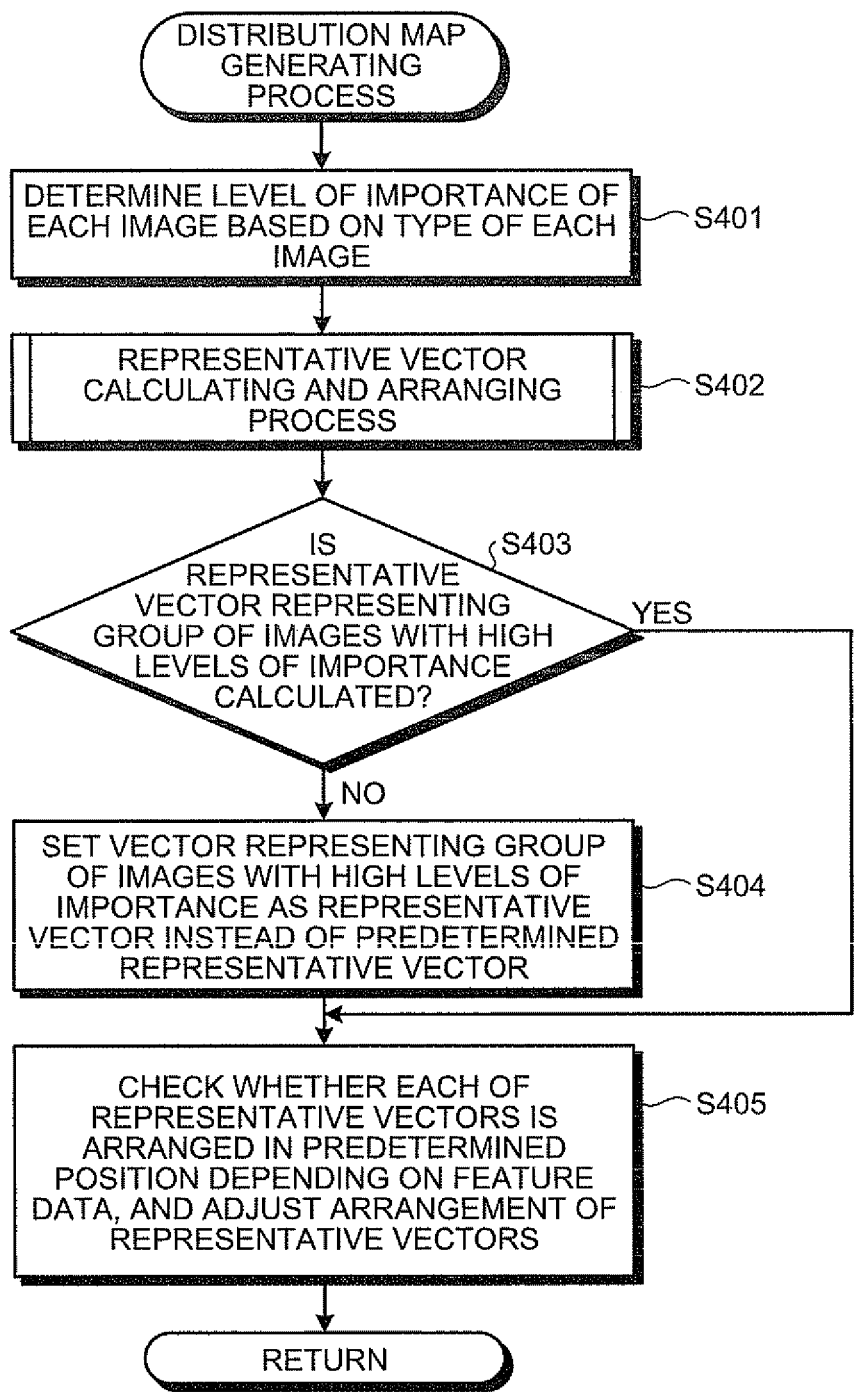
FIG. 11 is a schematic flowchart of a procedure of a distribution map generating process.

Next, step S104 of the procedure of the image processing is explained below. At step S104, the control unit 40 controls the distribution map generator 54 to perform the process for generating a distribution map. FIG. 11 is a schematic flowchart of a procedure of the distribution map generating process at step S104.

The importance level determining unit 55 determines a level of importance of each image based on a type of each image (step S401). Thereafter, the representative vector calculator 56 and the representative vector arrangement determining unit 57 perform a process for calculating a predetermined number of representative vectors and arranging the representative vectors on a distribution map, using SON (Self Organized Maps) (step S402).

Thereafter, the representative vector calculator 56 checks whether a representative vector that represents a group of images with high levels of importance is calculated (step S403). When a representative vector that represents a group of images with high levels of importance is not calculated (NO at step S403), the representative vector calculator 56 sets, as a representative vector, a vector that represents a group of images with high levels of importance instead of a predetermined vector of the calculated representative vectors (step S404). Thereafter, or when a representative vector that represents a group of images with high levels of importance is calculated (YES at step S403), the representative vector arrangement determining unit 57 checks whether each of the representative vectors is arranged in a desirable position depending on feature data, adjusts arrangement of the representative vectors (step S405), and completes the distribution map generating process. The distribution map generator 54 generates a distribution map through the processes at steps S401 to S405.

The process at step S402 is explained below. First, SOM is explained below. SOM is one of neural networks and is a method of mapping a high-dimensional data on, for example, a two-dimensional map by competitive learning without teaching data in order to perform clustering. With SOM, an arbitrary number of representative vectors can be obtained from a high-dimensional feature space. The obtained representative vectors have a positional relationship and are output such that representative vectors having feature data close to each other are in neighboring positions. The SOM has an input layer and an output layer. Data about high-dimensional feature data obtained from an image is input to the input layer, a predetermined number of neurons that has a positional relationship are arranged in the output layer, and a two-dimensional map is generated. Each neuron retains, as a representative vector, a coupling coefficient to each piece of feature data. In the first embodiment, feature data of images of a group of sequential images are input to the input layer, a coupling coefficient of each neuron of the output layer is calculated as a representative vector, and a two-dimensional map is generated. The generated two-dimensional map is adjusted to generate a distribution map of the group of sequential images. Each neuron is provided with a coupling coefficient that has a component (feature data) of the same dimension as that of input data. In other words, when feature data X of each image is represented by Equation (1), a coupling coefficient $M_i$ is represented by Equation (2) where N is the number of neurons and is a numerical value that can be set beforehand by an operator.

$$X = (^1x, ^2x, ^3x, K, ^kx) \quad (1)$$

$$M_i = (^1m_i, ^2m_i, ^3m_i, K, ^km_i) \quad (2)$$

i=1,2,...,N

In a general learning process of SOM, coupling coefficients of a predetermined number of neurons are determined randomly, and a plurality of pieces of high-dimensional feature data are input to the input layer. One piece of the random data is selected, a winner neuron is determined that has a representative vector most close to a feature vector of the selected data, and updates the coupling coefficient of the winner neuron and a coupling coefficient of a neighboring neuron that neighbors to the winner neuron in the feature space. Thereafter, a process for inputting data to the input layer, a process for determining a winner neuron, and a process for updating feature data of each neuron are repeated until a completion condition is satisfied.

A winner neuron is determined based on input data X and a Euclidean distance of each neuron in the feature space. Specifically, as represented by Equation (3), a neuron about which a Euclidean distance between the input data X(t) and a neuron $M_i(t)$ is the smallest is set as a winner neuron with respect to the input data X(t). In Equation (3), t represents the number of learning of input data.

$$c = \arg\min_i \{\|X(t) - M_i(t)\|\} \quad (3)$$

The feature data of the winner neuron and the neighboring neuron are updated depending on a Euclidean distance between the input data and each neuron, a learning coefficient $\alpha(t)$ and a neighborhood function $h_{ci}(t)$.

$$M_i(t+1) = M_i(t) + \alpha(t) h_{ci}(t) [X(t) - M_i(t)] \quad (4)$$

The learning coefficient $\alpha(t)$ is a function that attenuates as the number of learning increases and is represented by the following Equation (5).

$$\alpha(t) = \alpha_0 \exp\left[-\frac{t}{\alpha_{coeff} \times t_{max}}\right] \quad (5)$$

The neighborhood function $h_{ci}(t)$ is a function that determines a neighboring neuron and in which the distance $\|r_i\text{-}r_c\|$ between the winner neuron and another neuron and the number t of learning are variables. The closer to the winner neuron, the larger the value that the neighborhood function $h_{ci}(t)$ takes is, so that the weight increases. The larger the number of learning is, the smaller the value that the neighborhood function $h_{ci}(t)$ takes is, so that the weight decreases. The neighborhood function $h_{ci}(t)$ is defined by, for example, a normal distribution function represented by Equation (7). Alternatively, various implementations can be adopted. By repeating the process based on Equation (7), the representative vector of each neurons is drawn by the input data, so that SON is formed.

$$h_{ci}(t) = h(\|r_i - r_c\|, t) \quad (6)$$

$$h_{ci}(t) = \exp\left[\frac{9 \times \|r_i - r_c\|^2}{2\sigma^2(t)}\right] \quad (7)$$

Figure 12:
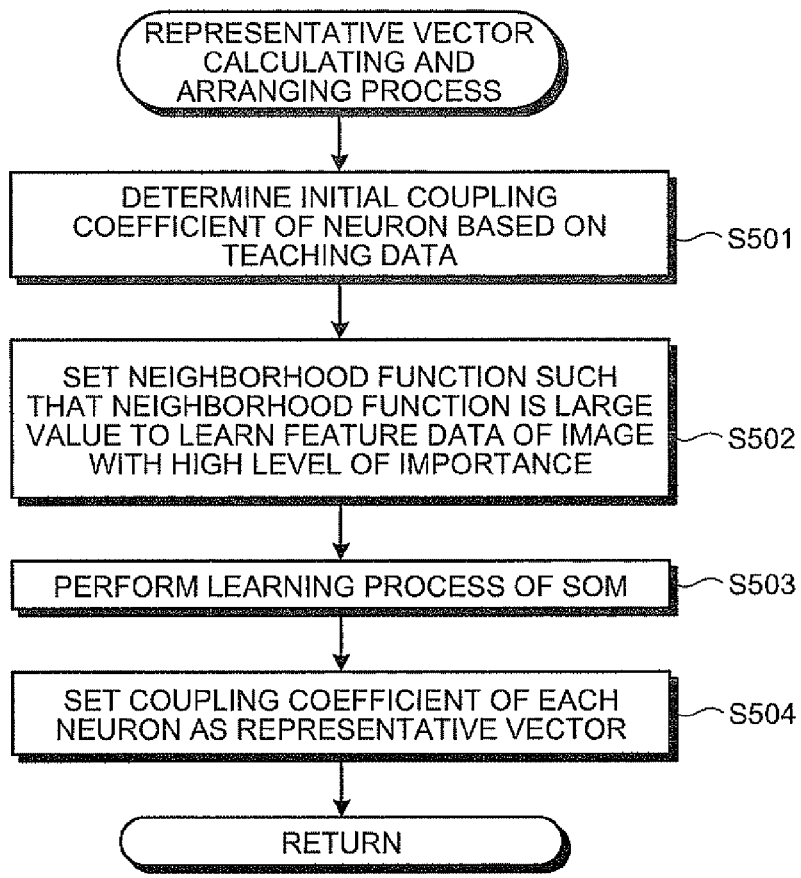
FIG. 12 is a schematic flowchart of a procedure of a representative vector calculating and arranging process.

At step S402, the representative vector calculator 56 and the representative vector arrangement determining unit 57 cooperatively perform the representative vector calculating and arranging process. FIG. 12 is a schematic flowchart of a procedure of the representative vector calculating and arranging process. The representative vector arrangement determining unit 57 determines an initial coupling coefficient of each neuron based on the teaching data, which is previously stored in the teaching data storage unit 31 (step S501). The representative vector calculator 56 sets the neighborhood function $h_{ci}(t)$ such that the neighborhood function $h_{ci}(t)$ is a large value to learn feature data of an image with a high level of importance (step S502). Thereafter, the representative vector calculator 56 and the representative vector arrangement determining unit 57 performs a learning process of SON (step S503), sets a coupling coefficient of each neuron as a representative vector and completes the process (step S504).

Figure 13:
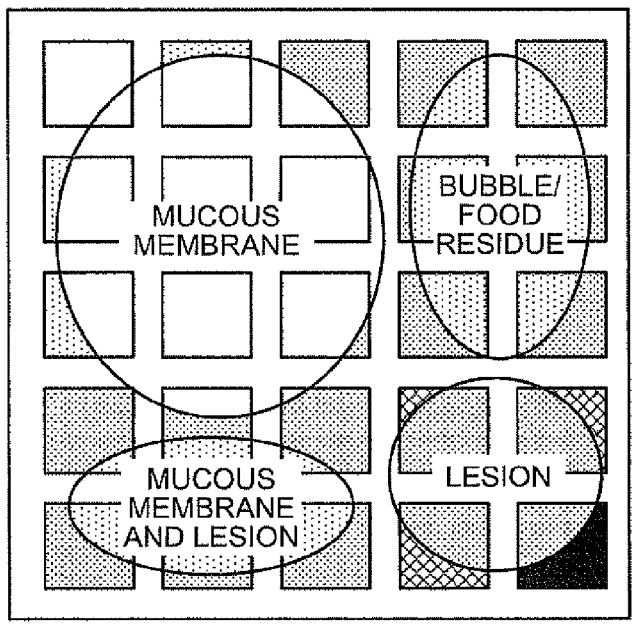
FIG. 13 is a diagram of an example of display of a distribution map.

In general SOM, an initial coefficient is provided randomly. In the first embodiment, the teaching data is provided as an initial coupling coefficient at step S501. This is because, when examining a group of sequential images that are taken by a capsule endoscope, it is desirable that images to be examined (such as a mucous membrane image or a lesion image) and a noise image (such as a food/residue image or a hole image) are separately distributed finally on the distribution map. For example, as shown in FIG. 13, a distribution map is generated in which a mucous membrane image is distributed in an upper left direction, a mucous membrane and lesion image is distributed in a lower left direction, a lesion image is distributed in a lower right direction, and bubble/food residue image is distributed in an upper right direction on a two-dimensional map.

In the first embodiment, an initial coupling coefficient is set from the teaching data to fix a trend of output position and prevent an important image from being missed. For example, the representative vector arrangement determining unit 57 provides a feature vector that represents feature data of the mucous membrane image from the teaching data as an initial coupling coefficient of the upper-left neuron (1,5) shown in FIG. 4. Similarly, the representative vector arrangement determining unit 57 provides a feature vector that represents feature data of the lesion image from the teaching data as an initial coupling coefficient of the lower-right neuron (5,1). In addition, the representative vector arrangement determining unit 57 provides a feature vector that represents feature data of the bubble/food residue image from the teaching data as an initial coupling coefficient of the upper-right neuron (5,5).

Next, learning of SOM is performed. Data is randomly selected from the input data, and the coupling coefficients of the neurons are updated. Because the initial coupling coefficients from the teaching data have been provided to the neurons, the coupling coefficients of the respective neurons are naturally drawn in the direction corresponding to the purposes. If the input data is important images, i.e., lesion images in this case, the smaller the number of important images in the weight function of Equation (6) is, the more the weight is increased compared with a normal case. Therefore, even when the absolute number of important images with respect to the overall input data is small, representative vectors that represent important images are left. After learning, the coupling coefficients of the respective neurons are set as representative vectors, and the coordinates of the respective neurons in the output layer are set as coordinates on the distribution map of the representative vectors.

The process at step S404 in the distribution map generating process is explained below. The process at step S404 is a process for assuredly calculating a representative vector that represents a group of images with high levels of importance. In the representative vector calculating and arranging process by SOM, a representative vector of a group of a smaller number of images with respect to the total number of images, for example, a representative vector of a group of lesion images may not be calculated. In the first embodiment, a level of importance of a lesion image is set higher to weigh feature data of the lesion image in the process by SOM. However, when the number of lesion images is small, a representative vector that represents a group of lesion images may not be calculated. Therefore, at step S404, a representative vector that represents images with high levels of importance is added instead of the representative vector that is calculated by SOM.

For example, the representative vector calculator 56 checks feature data of each of the calculated representative vectors. When there is not a vector that is close to feature data of an important image, the representative vector calculator 56 performs a process for newly generating a representative vector. An average of pieces of feature data of a group of lesion images is calculated as a new representative vector. The representative vector that represents a group of images most close to the lesion images from the representative vectors calculated by SOM, or a representative vector that is arranged in a predetermined position is replaced with the newly calculated representative vector. In this case, the feature data of representative vectors neighboring to the representative vector to be replaced are updated as well. For example, an average of pieces of feature data of the representative vector deleted by the replacement and the neighboring representative vectors is set as the feature data of each of the neighboring representative vectors, and the feature data of representative vectors that neighbor to the representative vectors whose feature data are updated are updated similarly. Accordingly, the feature data of a group of images represented by the deleted representative vector are also reflected to calculation of feature data of representative vectors.

In the process at step S405 in the distribution map generating process, the arrangement of the representative vectors are adjusted to assuredly arrange the representative vector that represents a predetermined type of image in a predetermined position. In many cases, representative vectors are arranged approximately on a distribution map as it is intended through the representative vector calculating and arranging process by SOM. However, an incorrect distribution may be formed in the learning process, and the representative vectors may be arranged in unintended positions. For this reason, after the process by SOM, the representative vector arrangement determining unit 57 checks the arrangement of the representative vectors, and adjusts and finally determines the arrangement of the vectors. For example, when a representative vector that represents a bubble/food residue image is in a mucous membrane area, a process is performed for replacing the representative vector with an amount of a representative vector that is close to an amount of mucous membrane in a bubble/food residue area. In other words, it is examined how much the feature data that represents the in-vivo environment, such as mucous membrane, lesion, villus, bubble, or food residue, is in each vector, and the representative vectors are sorted along an intended distribution.

Figure 14:
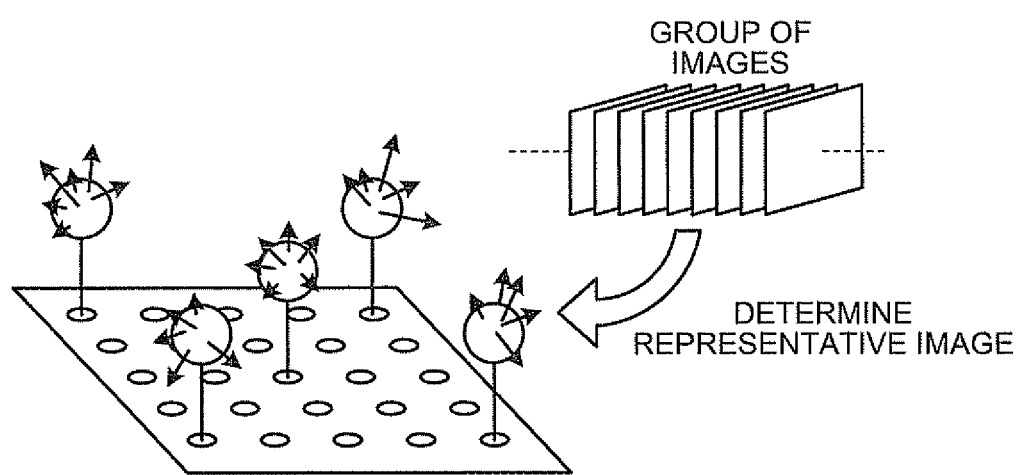
FIG. 14 is a schematic diagram of a relation between representative vectors and representative images.

Next, step S105 of the procedure of the image processing is explained below. At step S105, the display controller 41 arranges the representative images in the corresponding positions of the respective representative vectors and displays the representative images as a distribution map on the distribution map display unit 21 such that the observer can visually confirm the distribution map. In other words, the feature data of the respective vectors are compared with the images of the group of sequential images, which is input, and an image that has the closest feature data is arranged and displayed as a representative image of a representative vector on the distribution map. FIG. 14 is a schematic diagram of a relation between representative vectors and representative images. As shown in FIG. 14, each representative image is determined from a group of images that are similar to a corresponding representative vector.

Next, step S106 of the procedure of the image processing is explained below. At step S106, the operation accepting unit 11 accepts an operation for selecting a representative image through a GUI that is displayed on the distribution map display unit 21. In addition to the operation for selecting a representative image, the operation accepting unit 11 accepts an operation for performing a searching process and selecting an image to be displayed and a display mode.

Figure 15:
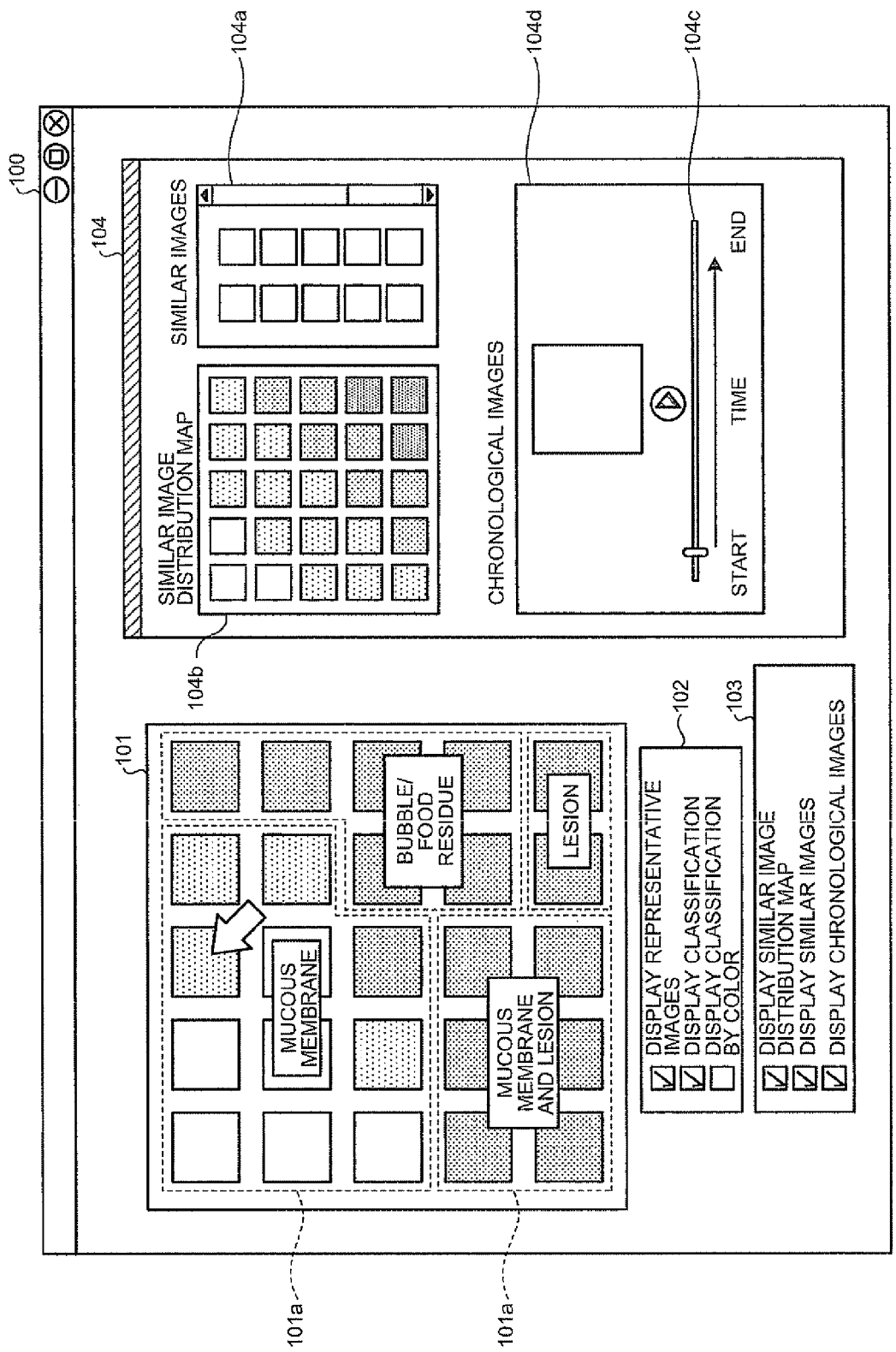
FIG. 15 is an explanatory view of an example of a display screen of a distribution map.

FIG. 15 is a diagram of an example of a display screen of the distribution map display unit 21. On an image display window 100 of the distribution map display unit 21, a distribution map 101, a distribution map display mode selection unit 102, a similar image distribution map selection unit 103, and a map 104 of images searched for are displayed.

Because the representative images that are selected corresponding to the representative vectors as represented in FIG. 14 and the types (mucous membrane, mucous membrane and lesion, lesion, bubble/food residue) of the representative images are displayed on the two-dimensional distribution map, the distribution map 101 represents an overall trend of the group of sequential images. Due to such display of the distribution map 101, the overall trend of the case is represented to the observer. In the first embodiment, by selecting "DISPLAY CLASSIFICATION" on the distribution map display mode selection unit 102, a result of classifying the representative vectors by the classifying unit 53 is superposed on the images that are displayed as the distribution map 101 and is displayed as represented by a dotted frame line 101a. This clarifies which representative vector (representative image) is classified in which group.

To display the result of classification by the classifying unit 53 in a superposed manner on the distribution map 101, color display in, for example, RGB gradation may be used by selecting "DISPLAY CLASSIFICATION BY COLOR" on the distribution map display mode selection unit 102, instead of the mode represented by the frame line 101a. For example, the upper leftmost coordinates that are closest to mucous membrane on the distribution map 101 is set to (R, G, B)=(0, 255, 0), the upper rightmost coordinates where bubble/food residue congregates is set to (R, G, B)=(0, 0, 255), and the lower rightmost coordinates where lesion congregates is set to (R, G, B)=(255, 0, 0). The color of coordinates on the distribution map 101 is set as follows. A Euclidean distance between feature data of a representative vector that is arranged in corresponding coordinates and feature data of each of the representative vectors that are arranged on the upper left, on the upper right, and on the lower right is obtained. When the Euclidean distance is 0, a pixel value of a corresponding color is set to 255. The larger the distance is, the lower the pixel value of the corresponding color is set. In other words, the closer to the upper left it is, the closer to G=255 it is. The closer to the upper right it is, the closer to B=255 it is. The closer to the lower right it is, the closer to R=255 it is. This visually represents the overall trend in color gradation and represents, as a medium color, the representative vector that has a fuzzy feature data at, for example, the border of classification.

Display of a similar image distribution map, display of similar images, and display of sequential images can be arbitrarily selected and set through the similar image distribution map selection unit 103 on the image display window 100 represented in FIG. 15. A result of a process in response to an operation by the observer is displayed on a part of the map 104 of images searched for.

For example, when an observer, such as a doctor, wants to observe in detail a lesion that is displayed on the distribution map 101 when examining images, operations for selecting "DISPLAY SIMILAR IMAGES" and for selecting representative image part that displays the lesion image (see the pointer represented by the arrow shown in FIG. 15) are performed, so that the operation accepting unit 11 accepts an operation for selecting the representative image. Thereafter, the information about the coordinates (area) of the part of the selected representative image is sent to the similar image searching unit 61. Upon receiving such input information, the similar image searching unit 61 searches for similar images having feature data similar to those of their respective representative vectors that are arranged on the respective coordinates (areas) selected on the distribution map 101 from the group of sequential images stored in the storage unit 30, and displays the similar images thus searched for on a similar image column 104a in the map 104 of images searched for.

When "DISPLAY SIMILAR IMAGE DISTRIBUTION MAP" is selected, the distribution map generator 54 generates a distribution map of a group of a plurality of similar images searched for by the similar image searching unit 61 according to the above-describes process procedure. Under the control of the display controller 41, the generated distribution map of similar images is displayed on a similar image distribution map column 104b in the map 104 of images searched for. This makes it possible to know the trend of the group of images in the limited range of the group of similar images, unlike the initial case where the all images of the group are targets.

In contrast, when "DISPLAY CHRONOLOGICAL IMAGES" is selected and the operation for selecting a representative image part that displays a lesion image of interest is performed, the operation accepting unit 11 accepts the operation for selecting a representative image. Thereafter, the information about the coordinates (or the range) of the selected representative image part is sent to the chronological image searching unit 62. Upon receiving receives input of such information, the chronological image searching unit 62 searches the group of sequential images stored in the storage unit 30 for the representative image that is most similar to the feature data of the representative vector arranged on the sleeted coordinates (range) on the distribution map 101 and a predetermined number of images that are chronologically close to the representative image. The chronological image searching unit 62 sequentially displays one by one the representative image searched for and the chronologically-close images chronologically on a similar image column 104d in the map 104 of images searched for with a display of a time bar 104c. Thus, the limited images prior and anterior to the representative image of interest can be appropriately observed.

As described above, in the first embodiment, the image distribution that visually represents overall features of the case is displayed as the distribution map 101 based on the group of sequential images that are taken by the capsule endoscope. Therefore, a ratio of images of mucous membrane, lesion, bubble/food residue with respect to the group of all images can be visually known at a glance. This reduces the work of an observer, such as a doctor, during image observation.

(Second Embodiment)

An image processing apparatus according to a second embodiment is explained below with reference to FIGS. 16 to 21. In the first embodiment, SOM is used for the distribution map generating process by the distribution map generator 54 to achieve in parallel a representative vector calculating function and a representative vector arrangement determining function. In the second embodiment, principal component analysis is used for the distribution map generating process of the distribution map generator 54. The processes other than that performed by the distribution map generator 54 are same as those of the first embodiment. The principal component analysis is a method of obtaining an arbitrary low-dimensional feature space from a high-dimensional feature space. In the principal component analysis, a straight line in a direction of the largest extension in an input distribution is set as a primary principal component and a straight line that is orthogonal to the primary principal component in a direction of the second largest extension is set as a secondary principal component. Thereafter, calculation is similarly carried out to an arbitrary low dimension (see, for example, "DIGITAL IMAGE PROCESSING (GC-ARTS Association)".

Figure 16:
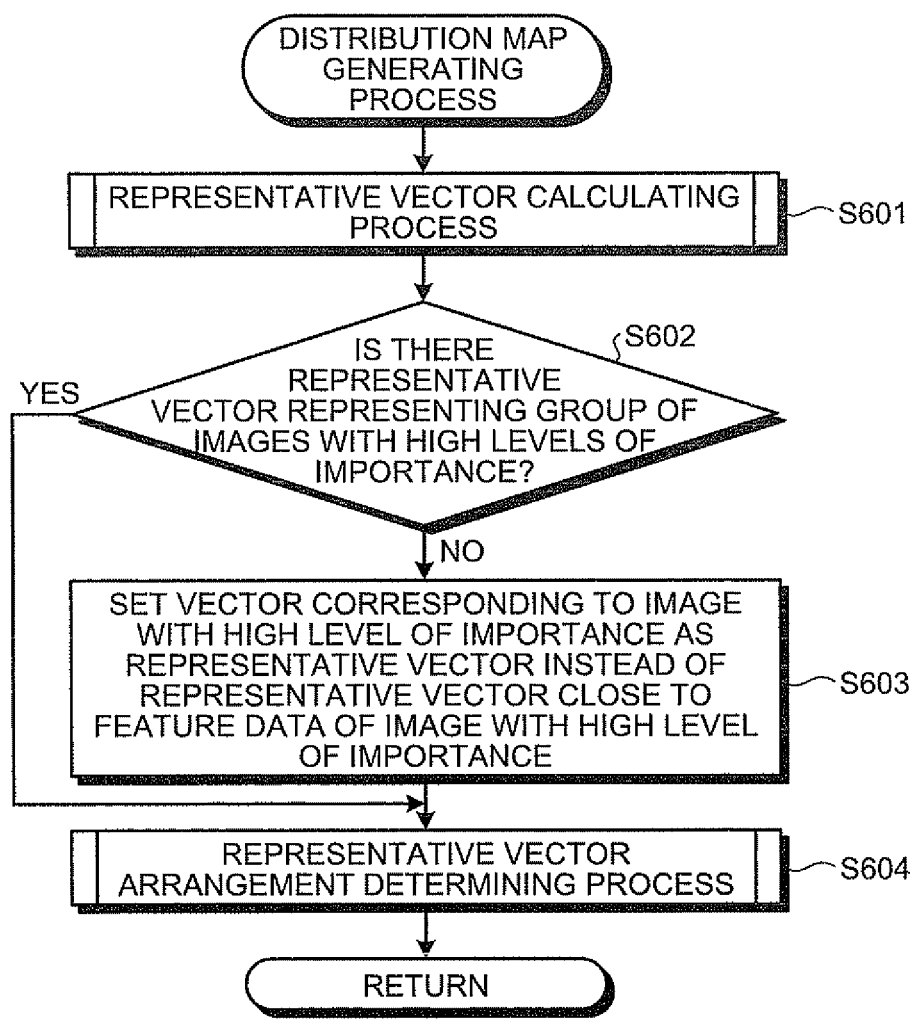
FIG. 16 is a schematic flowchart of a procedure of a distribution map generating process according to a second embodiment of the present invention.

FIG. 16 is a schematic flowchart of a procedure of a distribution map generating process at step S104 according to the second embodiment. First, the representative vector calculator 56 calculates representative vectors by the principal component analysis on a group of sequential images, which is input (step S601). The representative vector calculator 56 checks whether there is a representative vector that represents a group of images with high levels of importance (step S602). When there is not a representative vector that represents a group of images with high levels of importance (NO at step S602), the representative vector calculator 56 sets as a representative vector a vector corresponding to an image with a high level of importance instead of the representative vector that is close to feature data of the image with a high level of importance (step S603). Thereafter, or when there is a representative vector that represents a group of images with high levels of importance (YES at step S602), the representative vector arrangement determining unit 57 performs a process for determining arrangement of each of the calculated representative vectors on a distribution map (step S604) and completes the distribution map generating process. The distribution map generator 54 generates a distribution map through the processes from steps S601 to S604.

Figure 17:
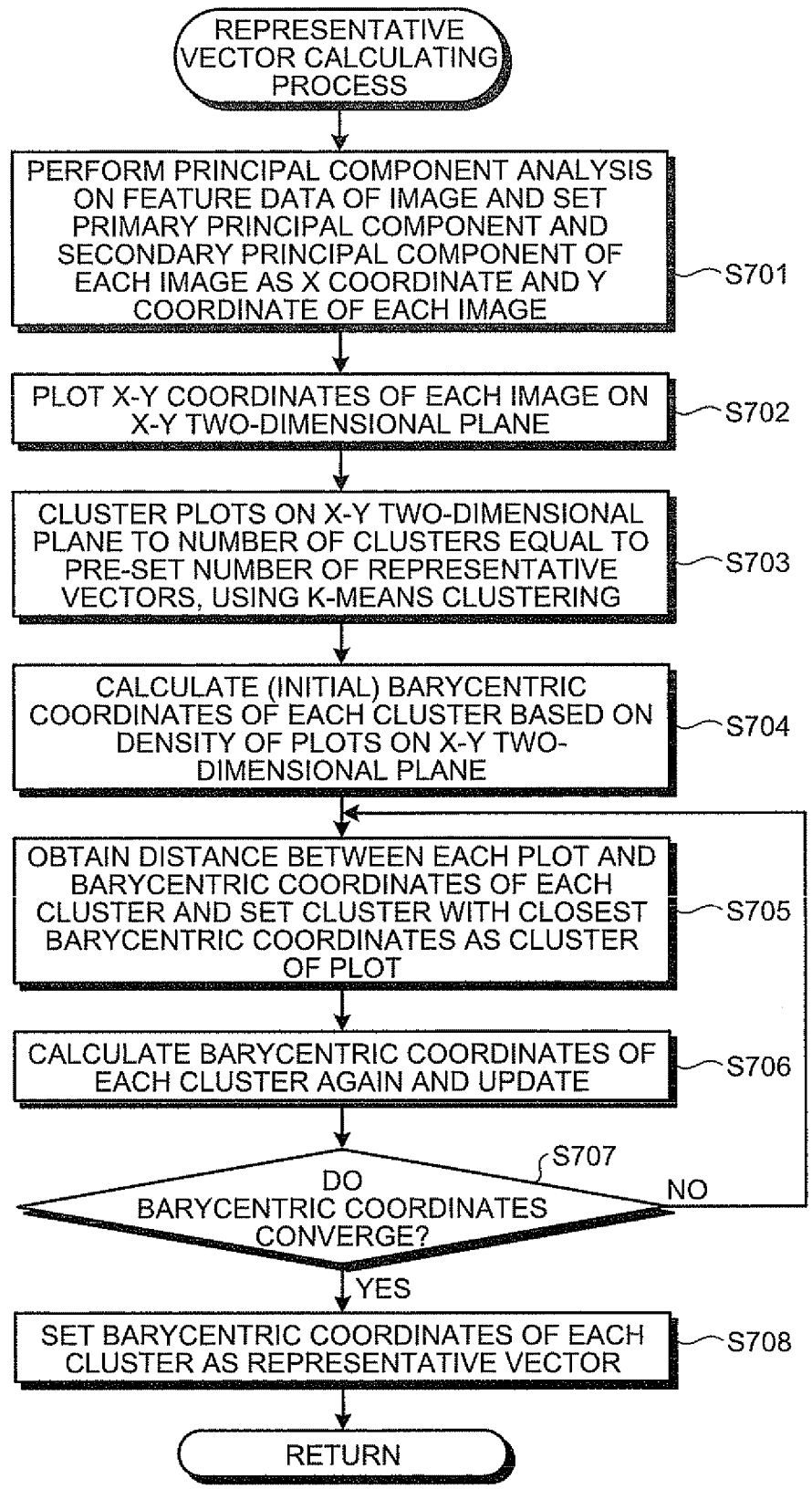
FIG. 17 is a schematic flowchart of an example of a representative vector calculating process.

The representative vector calculating process at step S601 is explained below. FIG. 17 is a schematic flowchart of an example of the representative vector calculating process at step S601. First, principal component analysis is performed. In the second embodiment, principal component analysis is performed on feature data of each image, and an X coordinate and a Y coordinate of each image are determined from a primary principal component and a secondary principal component (step S701). The coordinates of each image are plotted on an X-Y two-dimensional plane (step S702).

Figure 18:
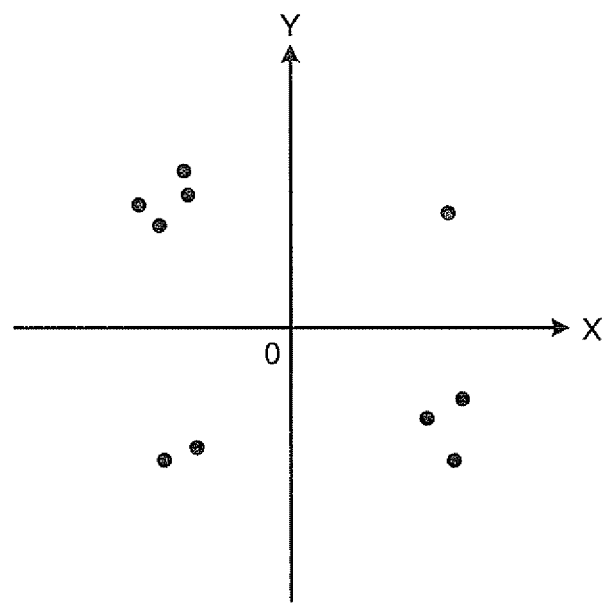
FIG. 18 is a schematic diagram of an example in which coordinates of each image are plotted on an X-Y two-dimensional plane according to a result of principal component analysis.

For example, FIG. 18 represents an example in which principal component analysis is performed from the feature data of 10 images and coordinates of each image are plotted on an X-Y two-dimensional plane. Through the principal component analysis, images whose feature data are close to each other are plotted in neighboring coordinate positions on the X-Y two-dimensional plane.

Subsequently, the plots on the X-Y two-dimensional plane are clustered to the number of clusters equal to a pre-set number of representative vectors, using K-means clustering (step S703). The larger the number of representative vectors is, the more a detailed distribution can be obtained. For this reason, the number of representative vectors may be determined depending on the size of the distribution map display unit 21 on which a distribution map is finally represented or the preference of the user.

In the clustering process using the K-means clustering, a plot density per unit area on the X-Y two-dimensional plane is obtained first and coordinates of clusters proportional to the obtained density are determined randomly in a unit area, so that initial barycentric coordinates of each cluster are determined (step S704). If all coordinates are randomly determined without consideration for plot density, clustering classification may not be appropriately carried out.

Figure 19:
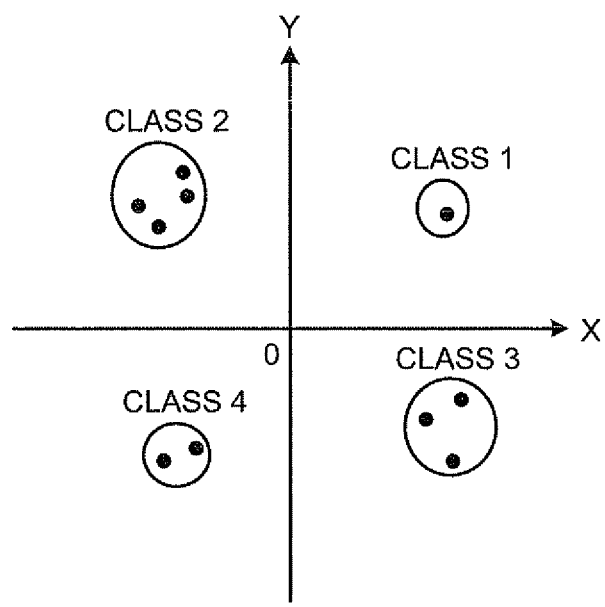
FIG. 19 is a schematic diagram that represents how barycentric coordinates of each cluster and plots contained in each cluster are determined.

Subsequently, a distance between each plot and barycentric coordinates of each cluster are obtained, and the cluster with the closest barycentric coordinates is set as a cluster of the plot (step S705). Then, barycentric coordinates of all plots that belong to each cluster are newly calculated (step S706). In this case, the barycentric coordinates are calculated as average coordinates of barycentric coordinates of the plots. The barycentric coordinates of each cluster are updated by the newly calculated barycentric coordinates. Thereafter, until barycentric coordinates of each cluster converge (Yes at step S707), the processes from steps S705 and S706 are repeated. Through repetition of such processes, the barycentric coordinates of each cluster and plots contained in each cluster are determined. FIG. 19 is a schematic diagram that represents how such determination is made.

Figure 20:
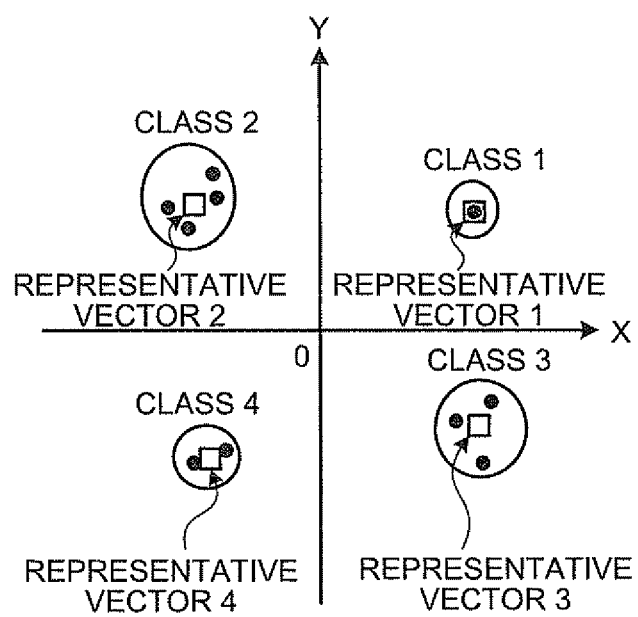
FIG. 20 is a schematic diagram that represents how it is defined that barycentric coordinates of each cluster on an X-Y two-dimensional plane that is calculated from K-means clustering is a representative vector.

It is defined that the barycentric coordinates of each cluster on the X-Y two-dimensional plane, which are calculated based on the K-means clustering, are a representative vector on a distribution map (step S708). FIG. 20 is a schematic diagram representing this situation.

Figure 21:
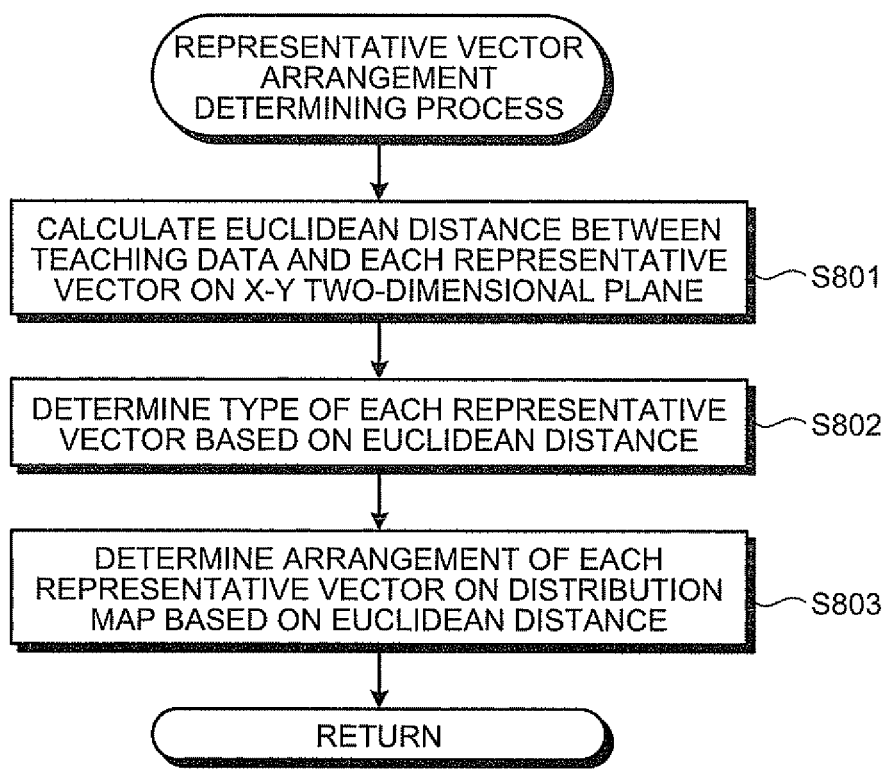
FIG. 21 is a schematic flowchart of an example of a representative vector arrangement determining process.

The representative vector arrangement determining process at step S604 is explained below. FIG. 21 is a schematic flowchart of an example of the representative vector arrangement determining process for determining arrangement of representative vectors on the distribution map at step S604. Prior to this process, the classifying unit 53 classifies the type of each representative vector from feature data of each representative vector and teaching data. According to the classification, representative vectors that represent a mucous membrane image, a lesion image, and a bubble/food residue image are arranged on the upper left, on the lower right, and on the upper right, respectively, on the distribution map of the X-Y two-dimensional plane, as in the case represented in FIG. 4. A Euclidean distance is calculated from each representative vector on the X-Y two-dimensional plane and feature data of the teaching data (step S801). Based on the Euclidean distance, a type of each representative vector is determined (step S802). Based on the value of the calculated Euclidean distance, arrangement coordinates of each representative vector on the distribution map is determined (step S803). For example, the smaller the Euclidean distance between a representative vector in a mucous membrane area and the teaching data of a mucous membrane image is, the closer to the upper left coordinates on the distribution map it is.

The representative vectors congregate in an area where the image plot density is high on the X-Y two-dimensional plane. For this reason, after sorting of arrangement of the representative vectors is carried out based on the feature data, a process for correcting the coordinates such that the representative vectors are uniformly arranged on the distribution map is performed. Thus, an intended distribution map that represents the overall trend is output as in the case of the first embodiment.

The above and other features, advantages and technical and industrial significance of this invention will be better understood by reading the following detailed description of presently preferred embodiments of the invention, when considered in connection with the accompanying drawings.

What is claimed is:
1. An image processing apparatus, comprising:
a processor; and
a storage unit storing a group of sequential images that are taken by an image taking apparatus;
wherein the processor is configured to interact with the storage unit to calculate feature data of each image contained in the group of sequential images;
wherein the processor is configured to interact with the storage unit to generate, by a learning process using the feature data of each image, a distribution map that represents an overall trend of the group of sequential images;
wherein the processor is configured to interact with the storage unit to display the distribution map on a display unit;
wherein the processor, when configured to generate the distribution map, is configured to calculate a predetermined number of representative vectors that represent a plurality of images contained in the group of sequential images, during the learning process using the feature data of each image, based on the feature data of each image and a level of importance of each image by giving more weight in the learning process to the feature data of an important image than the feature data of the other images when the important image has a level of importance higher than a predetermined value; and
wherein the processor is configured to determine arrangement of the calculated representative vectors on the distribution map.
2. The image processing apparatus according to claim 1, wherein the processor, when configured to generate the distribution map, is configured to determine the level of importance of each image, using the feature data and teaching data.

3. The image processing apparatus according to claim 2, wherein:
the group of sequential images is a group of chronological images taken by the in-vivo image taking apparatus that is introduced into a body of a subject; and
the processor, when configured to determine the importance level, is configured to determine that a level of importance of a lesion image is high, and to determine that a level of importance of a bubble/food residue image is low.

4. The image processing apparatus according to claim 1, wherein the processor, when configured to determine the representative vector arrangement, is configured to determine arrangement of the representative vectors such that representative vectors whose feature data are similar to each other are in neighboring positions on the distribution map.

5. The image processing apparatus according to claim 1, wherein the processor, when configured to calculate the predetermined number of representative vectors, is configured to reduce or increase a number of representative vectors of each of a plurality of groups of images with similar feature data, depending on a number of images of each of the groups of images.

6. The image processing apparatus according to claim 1, wherein
the processor, when configured to generate the distribution map, is configured to classify each image or each of the representative vectors into a type corresponding to a state of an image-taking target based on the feature data; and
the processor, when configured to determine the representative vector arrangement, is configured to determine the arrangement of the representative vectors based on their respective types of the classified representative vectors.

7. The image processing apparatus according to claim 6, wherein the processor, when configured to determine the representative vector arrangement, is configured such that the arrangement of the representative vectors on the distribution map is previously specified depending on the respective types of the representative classified vectors.

8. The image processing apparatus according to claim 7, wherein the processor, when configured to control the display unit, is configured to display the distribution map superposed with a result of classification of the representative vectors.

9. The image processing apparatus according to claim 6, wherein the processor, when configured to control the display unit, is configured to display the distribution map superposed with a result of classification of the representative vectors.

10. The image processing apparatus according to claim 9, wherein:
the group of sequential images is a group of chronological images that are taken by the in-vivo image taking apparatus that is introduced into a body of a subject; and
the processor, when configured to calculate the feature data, is configured to calculate, as the feature data, numerical values that represent features of mucous membrane, lesion, villus, bubble, and food residue that are image taking targets unique to internal body.

11. The image processing apparatus according to claim 6, wherein:
the group of sequential images is a group of chronological images taken by the in-vivo image taking unit that is introduced into a body of a subject; and
the processor, when configured to classify, is configured to include, in the types into which each image or each of the representative vectors is classified based on feature data, at least one of a mucous membrane image, a lesion image, a mucous membrane/lesion image of normal mucous membrane and lesion, and a bubble/food residue image of bubble and food residue.

12. The image processing apparatus according to claim 1, wherein the processor, when configured to control the display unit, is configured to display the distribution map in which images whose feature data are most similar to feature data of their respective representative vectors are arranged in corresponding positions of the respective representative vectors as representative images.

13. The image processing apparatus according to claim 1, wherein the processor, when configured to control the display unit, is configured to display the distribution map in which colors corresponding to the feature data of their respective representative vectors are arranged in positions of the respective representative vectors.

14. The image processing apparatus according to claim 1, wherein:
the processor, when configured to calculate the feature data, is configured to divide each image into predetermined areas; and
the processor, when configured to calculate the feature data, is configured to calculate, as the feature data of each image, an assembly of numerical values that represent states of their respective divided areas.

15. The image processing apparatus according to claim 1:
wherein the processor is configured to interact with the storage unit to accept an operation for selecting arbitrary coordinates and range on the distribution map displayed on the display unit;
wherein the processor is configured to interact with the storage unit to search the group of sequential images for a predetermined image based on information about the coordinates or the range selected on the distribution map; and
wherein the processor, when configured to control the display unit, is configured to display the searched image on the display unit.

16. The image processing apparatus according to claim 15, wherein the processor, when configured to search the image, is configured to search for a similar image whose feature data is similar to feature data of a representative vector arranged in the selected coordinates or range on the distribution map.

17. The image processing apparatus according to claim 16, wherein:
the processor, when configured to generate the distribution map, is configured to generate the distribution map of a group of similar images searched for by the similar image searching unit; and
the processor, when configured to control the display unit, is configured to display the distribution map of the group of similar images on the display unit.

18. The image processing apparatus according to claim 15, wherein the processor, when configured to search for the predetermined image, is configured to search for a representative image that is an image most similar to feature data of a representative vector that is arranged in the selected coordinates or range on the distribution map and an image in a position chronologically close to the representative image.

19. The image processing apparatus according to claim 1, wherein the group of sequential images is a group of chronological images taken by the in-vivo image taking apparatus that is introduced into a body of a subject.

20. The image processing apparatus according to claim 1, wherein the processor, when configured to calculate the predetermined number of representative vectors, is configured to calculate original representative vectors and add one or more new representative vectors with respect to a group of images whose feature data are similar to the feature data of the important image, to the original representative vectors.

21. An image processing method, comprising:
    calculating feature data of each image contained in a group of sequential images that are taken by an image taking apparatus;
    generating, by a learning process using the feature data of each image, a distribution map that represents an overall trend of the group of sequential images, wherein the generating includes calculating a predetermined number of representative vectors that represent a plurality of images contained in the group of sequential images, during the learning process using the feature data of each image, based on the feature data of each image and a level of importance of each image by giving more weight in the learning process to the feature data of an important image than the feature data of the other images when the important image has a level of importance higher than a predetermined value;
    displaying the distribution map on a display unit; and
    determining arrangement of the calculated representative vectors on the distribution map.

22. A computer program product having a computer readable storage unit storing programmed instructions, wherein the instructions, when executed by a computer, cause the computer to perform:
    calculating feature data of each image contained in a group of sequential images that are taken by an image taking apparatus;
    generating, by a learning process using the feature data of each image, a distribution map that represents an overall trend of the group of sequential images, wherein the generating includes calculating a predetermined number of representative vectors that represent a plurality of images contained in the group of sequential images, during the learning process using the feature data of each image, based on the feature data of each image and a level of importance of each image by giving more weight in the learning process to the feature data of an important image than the feature data of the other images when the important image has a level of importance higher than a predetermined value;
    displaying the distribution map on a display unit; and
    determining arrangement of the calculated representative vectors on the distribution map.

* * * * *